US009808415B2

(12) United States Patent
Gamez-Garcia et al.

(10) Patent No.: US 9,808,415 B2
(45) Date of Patent: Nov. 7, 2017

(54) POLYOXYALKYLENE SUBSTITUTED ALKYLENE DIAMINES AND THEIR USE ON SKIN AND HAIR

(71) Applicant: BASF SE, Ludwigshafen (DE)

(72) Inventors: Manuel Gamez-Garcia, New City, NY (US); Joel Basilan, Bloomfield, NJ (US); Amber Octavia Evans, Elmsford, NY (US); Heather Lee Bochnovich, Flemington, NJ (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/416,131

(22) PCT Filed: Aug. 15, 2013

(86) PCT No.: PCT/US2013/055096
§ 371 (c)(1),
(2) Date: Jan. 21, 2015

(87) PCT Pub. No.: WO2014/028709
PCT Pub. Date: Feb. 20, 2014

(65) Prior Publication Data
US 2015/0320659 A1  Nov. 12, 2015

Related U.S. Application Data

(60) Provisional application No. 61/683,763, filed on Aug. 16, 2012, provisional application No. 61/782,876, filed on Mar. 14, 2013.

(51) Int. Cl.
*A61Q 5/06* (2006.01)
*A61Q 5/12* (2006.01)
*A61Q 19/00* (2006.01)
*A61Q 19/10* (2006.01)
*A61K 8/86* (2006.01)
*A61Q 17/04* (2006.01)
*A61Q 9/02* (2006.01)
*A61Q 3/00* (2006.01)
*A61K 8/41* (2006.01)

(52) U.S. Cl.
CPC .............. *A61K 8/86* (2013.01); *A61K 8/41* (2013.01); *A61Q 3/00* (2013.01); *A61Q 5/06* (2013.01); *A61Q 5/12* (2013.01); *A61Q 9/02* (2013.01); *A61Q 17/04* (2013.01); *A61Q 19/00* (2013.01); *A61Q 19/002* (2013.01); *A61Q 19/10* (2013.01); *A61K 2800/40* (2013.01); *A61K 2800/5426* (2013.01)

(58) Field of Classification Search
None
See application file for complete search history.

(56) References Cited

U.S. PATENT DOCUMENTS

| | | | |
|---|---|---|---|
| 3,954,960 A * | 5/1976 | Valan | A61K 8/8182 424/47 |
| 5,209,865 A | 5/1993 | Winterton | |
| 5,213,793 A * | 5/1993 | Moses | A61K 8/416 132/202 |
| 5,641,480 A | 6/1997 | Vermeer | |
| 5,648,323 A | 7/1997 | Coffindaffer et al. | |
| 5,709,847 A | 1/1998 | Bissett et al. | |
| 5,733,536 A | 3/1998 | Hill et al. | |
| 6,409,998 B1 | 6/2002 | Candau et al. | |
| 6,616,935 B1 | 9/2003 | Bengs et al. | |
| 6,878,695 B2 | 4/2005 | Woo et al. | |
| 6,979,439 B1 * | 12/2005 | Sakai | A61K 8/342 424/70.1 |
| 7,179,880 B2 | 2/2007 | Kawa et al. | |
| 7,459,417 B2 | 12/2008 | Derici et al. | |
| 7,611,698 B2 | 11/2009 | Derici et al. | |
| 2003/0084519 A1* | 5/2003 | Yang | A61K 8/375 8/405 |
| 2004/0197292 A1 | 10/2004 | Kaczvinsky et al. | |

(Continued)

FOREIGN PATENT DOCUMENTS

| | | |
|---|---|---|
| CN | 1665470 A | 9/2005 |
| CN | 1665471 A | 9/2005 |
| CN | 1665472 A | 9/2005 |

(Continued)

OTHER PUBLICATIONS

International Search Report dated Nov. 22, 2013.
International Preliminary Report on Patentability dated Feb. 17, 2015.
Schmolka, Irving R., Journal of the American Oil Chemists Society, 1977, vol. 54, No. 3 pp. 110-116.
Hamley, Ian W. et al., Developments in block copolymer science and technology, 2004 pp. 324-340.

*Primary Examiner* — Jyothsna Venkat
(74) *Attorney, Agent, or Firm* — Lowenstein Sandler LLP

(57) ABSTRACT

This application is directed to hair and skin conditioning compositions which contain specific polyoxyalkylene substituted alkylene diamines. The polyoxyalkylene substituted alkylene diamines function as conditioning agents on hair and skin via cloud point deposition. The polyoxyalkylene substituted alkylene diamines in addition to functioning as conditioning agents on skin and hair by themselves also function to enhance deposition of lipophilic benefit agents such as for example fatty alcohols, esters of fatty acids, hydrophobic vitamin or vitamin complexes, natural or synthetic triglycerides including glyceryl esters and derivative, pearlescent waxes, hydrocarbon oils, siloxanes of silicones, perfume oils, super-fatting agents, water insoluble or slightly soluble organic sunscreens, micronized sunscreens, plant extracts, essential oils and hydrophobically modified pigments.

14 Claims, No Drawings

(56) References Cited

U.S. PATENT DOCUMENTS

2006/0057097 A1    3/2006  Derici et al.

FOREIGN PATENT DOCUMENTS

| CN | 1767803 A | 5/2006 |
|---|---|---|
| DE | 29 18 380 A1 | 11/1979 |
| EP | 1093796 A1 | 4/2001 |
| EP | 1 505 949 B1 | 2/2007 |
| EP | 1 503 724 B1 | 4/2009 |
| EP | 1 503 723 B1 | 6/2009 |
| GB | 1494915 A | 12/1977 |
| JP | 05-51874 | 3/1993 |
| WO | 00/25731 A1 | 5/2000 |
| WO | 01/85124 A1 | 11/2001 |
| WO | 02/39974 A1 | 5/2002 |
| WO | 03/041675 A2 | 5/2003 |
| WO | 03/041676 A1 | 5/2003 |
| WO | 03/106522 A1 | 12/2003 |

* cited by examiner

POLYOXYALKYLENE SUBSTITUTED ALKYLENE DIAMINES AND THEIR USE ON SKIN AND HAIR

This is a National Phase Application filed under 35 U.S.C. 371 of International Application No. PCT/US2013/055096, filed Aug. 15, 2013, claiming the benefit under 35 USC 119(e) of U.S. Provisional Application Nos. 61/782,876, filed Mar. 14, 2013 and 61/683,763, filed Aug. 16, 2012 the entire contents of each of which is hereby incorporated herein by reference in its entirety.

TECHNICAL FIELD OF THE INVENTION

The invention is directed to hair and skin conditioning compositions which contain specific polyoxyalkylene substituted alkylene diamines. In particular this application is concerned with hair or skin conditioning compositions for rinse off or leave on, preferably rinse off, applications which are applied to hair or skin after washing, shampooing or conditioning. Furthermore, the compositions are directed to methods of improving deposition of emollients and hydrophobic benefit agents to skin or hair via use of the same polyoxyalkylene substituted alkylene diamines.

BACKGROUND

Hair conditioner compositions which provide conditioning to the hair are well known in the art. The purpose of the conditioning agent is to make the hair easier to comb when wet and more manageable when dry, e.g. less frizzy, less friction in dry, and less static "fly-away". Conditioners also make the hair feel softer. Typically, these conditioning agents are either water-insoluble oily materials such as silicones which act by spreading on the hair in the form of a film, or cationic surfactant materials or polymers, which adsorb onto the hair surface.

The cationic conditioning materials for hair and skin are frequently based on the affinity of quaternized nitrogen for keratinous substrates. This affinity results from an electrostatic interaction between positively charged alkyl nitrogen quaternary compounds and the negative sites on hair or skin surfaces. This electrostatic interaction helps to retain the cationic conditioner on the hair or skin surface and resist wash off. However, the presence of cationic conditioners often causes formulation difficulties in particular with anionic detersive surfactants which are frequently present in such products as shampoos and shower gels.

Additionally, as cationic conditioning agents are substantive to skin and hair via electrostatic attraction, these cationic compounds may actually interfere with the deposition of emollients and hydrophobic benefit agents onto keratinous substrates. Accordingly, there is a need for conditioning agents which are substantive to hair and skin but do not carry a positive charge. Furthermore, there is a need for conditioning agents whose conditioning effects can be controlled during application and rinsing to provide effects that vary from very light to heavy as needed and have the capacity to deliver hydrophobic ingredients to keratin surfaces from rinse-off or leave-on applications.

Polyoxyalkylene substituted alkylene diamines are known surfactants for use in hair compositions. For example, U.S. Pat. Nos. 7,611,698, 7,459,417, 5,648,323, 5,709,847, 5,641,480, 5,733,536 and its International Application No., WO03/106522 teach the use of polyoxyalkylene substituted alkylene diamines not as conditioning agents but rather as nonionic surfactants that aid in the solubilization, co-solubilization, and stabilization of hair or skin formulations.

In the patents or applications referred to above, the polyoxyalkylene substituted alkylene diamines are taught to be used as non-ionic surfactants only. There is no recognition by the prior art that a very particular class of polyoxylakylene substituted alkylene diamines might be useful in themselves as conditioning agents or that the polyoxyalkylene substituted alkylene diamines could be made substantive to hair or skin via a phase inversion mechanism. Additionally, there was no recognition that certain polyoxyalkylene substituted alkylene diamines would further be capable of depositing hydrophobic actives or emollients onto skin and hair or reducing the drying time of hair.

SUMMARY OF THE INVENTION

The Applicant has discovered that a particular class of polyoxyalkylene substituted alkylene diamines achieve the desired effects mentioned above, that is, they are substantive to skin or hair under ambient conditions, they provide emolliency, conditioning to hair or skin and they are capable of depositing additional benefit agents such as silicones, triglycerides, waxes, fragrances, and the like.

While not wishing to be bound by theory, it is believed that the particular compounds of formula (I) and (II) below condition hair and/or skin at least partially by a mechanism involving cloud point deposition. The polyoxyalkylene substituted diamines mentioned above belong to the class of non-ionic polymeric surfactants and as such they form either direct or inverse micelles or polymeric micelles in water depending on their composition. When the hydrophobic/lipophilic balance (HLB) of these compounds is appropriate they form inverse micelles or polymeric micelles via clouding point phenomena. It has been found that these hydrophobic polymeric micelles show a high level of affinity to keratin surfaces thus providing conditioning and deposition effects on hair or skin.

As can be seen the compounds of formula (I) and (II) are amphiphilic. The ethyleneoxide blocks providing hydrophilic properties and the propylene oxide blocks providing hydrophobic properties to the molecule. As a result of this amphiphilic character the compounds solubility in water or oil changes substantially with temperature and/or with their water dilution ratio. The particular compounds of formula (I) and (II) above become insoluble or less soluble in aqueous compositions at the temperature of use, ie. when washing or rinsing hair or skin at temperatures above ambient. As the cloud point is reached or exceeded, the compounds undergo a process of phase separation. That is the compounds aggregate so that they reorient their hydrophobic and hydrophilic blocks to form inverse polymeric micelles or oil like droplets which separate from the water phase and deposit onto the keratinous surface. Thus the compounds form a lubricious, emollient like film on hair or skin via cloud point deposition. It is believed that this mechanism also is responsible for deposition of hydrophobic benefit agents onto skin or hair.

Accordingly, one embodiment claimed herein is an aqueous hair or skin conditioner comprising a compound of formula (I) or formula (II)

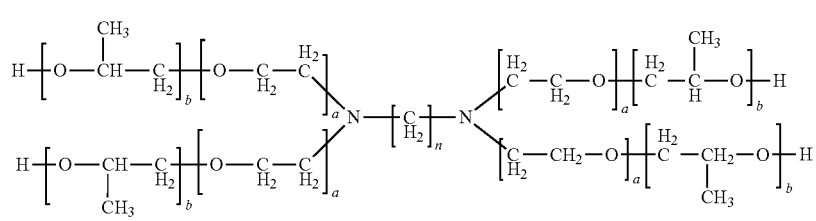

Formula (I)

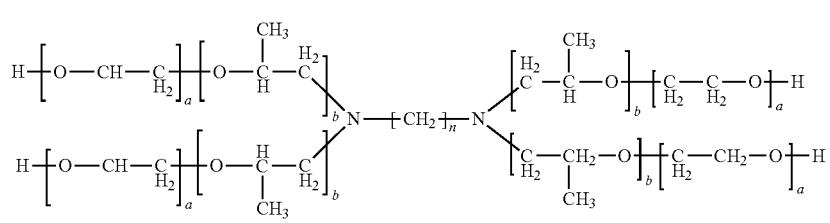

Formula (II)

wherein
a and b are repeat units based on ethylene oxide and propylene oxide respectively;
n is 1-4, preferably n is 2;
the "a" repeat units makes up about 5 to about 50, preferably about 10 to about 45 and most preferably from about 15 to about 40 wt. % and the wt. % is based on the total weight of the sum of a and b repeat units and the cloud point for formula (I) and formula (II) is less than 100° C., which composition optionally further contains cosmetic adjuvants or carriers suitable for use on skin or hair.

The hair or skin conditioning composition will optionally further contain cosmetic adjuvants or carriers or combinations suitable for use on skin or hair.

Furthermore, the use of formula (I) and/or formula (II) as a delivery system for hydrophobic benefit agents onto a keratinous substrate is envisioned. Also use of formula (I) and/or formula (II) as a conditioning agent or system for hair or skin is envisioned. The delivery system and conditioning effects are implemented via cloud point deposition.

A method of conditioning a keratinous substrate is also disclosed wherein the substrate is treated with an aqueous composition comprising a compound of formula (I) or (II) as described above at a temperature exceeding or at the cloud point of formula (I) or (II).

Additionally, a method of depositing a hydrophobic benefit agent onto a keratinous substrate is disclosed comprising the step of treating the substrate with an aqueous composition comprising the compound of formula (I) and/or formula (II) and a hydrophobic benefit agent, wherein the treatment is carried out at or above the cloud point of formula (I) and/or formula (II).

The hydrophobic benefit agent is preferable defined as selected from the group consisting of fatty alcohols, esters of fatty acids, hydrophobic vitamin or vitamin complexes, natural or synthetic triglycerides including glyceryl esters and derivative, pearlescent waxes, hydrocarbon oils, siloxanes or silicones, perfume oils, super-fatting agents, water insoluble or slightly soluble organic sunscreens, micronized sunscreens, plant extracts, essential oils and hydrophobically modified pigments.

Furthermore, a hydrophobic benefit agent delivery system to a keratinous substrate is envisioned comprising an aqueous composition comprising a compound of formula (I) or (II) as described above and a hydrophobic benefit agent at the cloud point of formula (I) or (II).

Lastly a method of reducing the drying time of hair is envisioned comprising the steps of applying to the hair an aqueous composition comprising a compound of formula (I) or (II) and optionally a hydrophobic benefit agent and drying, especially blow drying of hair wherein preferably the cloud point for formula (I) and formula (II) is less than 100° C., which composition optionally further contains cosmetic adjuvants or carriers suitable for use on skin or hair.

DETAILED DESCRIPTION OF THE INVENTION

Amphiphilic

Amphiphilic for purposes of this application means having both hydrophobic and hydrophilic characteristics. In reference to formula (I) and (II), the "a" repeat units are ethylene oxide units and have good water solubility thus they are considered hydrophilic. The "b" repeat units are propylene oxide units and have by comparison to ethylene oxide low water solubility and are thus considered hydrophobic.

The terms "hydrophobic" and "hydrophilic" are used in their ordinary sense. That is, hydrophilic, when it refers to a polymer or a repeat unit, means that the polymer or repeat unit has a strong tendency to bond with or absorb water, which can result in solutions of the polymer or swelling and/or formation of a gel. This property is characteristic of polymers prepared from polar monomers or condensants. Similarly, hydrophobic means that the polymer or repeat unit is antagonistic to water and generally cannot be dissolved in or swelled by water. This property is characteristic of polymers or repeat units prepared from relatively non-polar monomers Repeat Unit Repeat unit is used in the ordinary sense. For example, the ethylene oxide repeat unit means

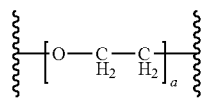

will be repeated "a" times or in the case of propylene oxide,

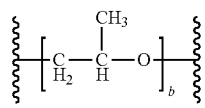

will be repeated "b" times.

Degree of Polymerization

Degree of polymerization means the number of repeat monomer units making up a polymer. For example, if the degree of polymerization is 100, then 100 monomer units are incorporated into the polymer.

Comprising

Comprising for purposes of the invention is open ended, that is other components may be included. Comprising is synonymous with containing or including.

Percentages

All percentages, parts and ratios are based upon the weight unless otherwise specified. All such weights as they pertain to listed ingredients are based on the active level and, therefore, do not include carriers or by-products that may be included in commercially available materials, unless otherwise specified.

Aqueous

The conditioning compositions will normally contain water. The water content of the aqueous personal care conditioning compositions will range from about 10 wt. % to about 95 wt. %, preferably from about 20 or 25 wt. % to about 90 wt. % water, wherein the weight percent is based on the total weight of the personal care conditioning composition.

Molecular Weight

The term molecular weight will normally mean a weight average molecular weight ($M_w$) unless otherwise indicated.

Hydrophobic Benefit Agent

A hydrophobic benefit agent may be any water insoluble or lipophilic substance which benefits the keratinous substrate. Thus, for example, the benefit agent may be any material which retards the decrease in water content from skin (stratum corneum) or hair. Thus the hair or skin care composition may further contain hydrophobic benefit agents selected from the group consisting of fatty alcohols, esters of fatty acids, hydrophobic vitamin or vitamin complexes, natural or synthetic triglycerides including glyceryl esters and derivative, pearlescent waxes, hydrocarbon oils, siloxanes of silicones, perfume oils, super-fatting agents, water insoluble or slightly soluble organic sunscreens, micronized sunscreens, plant extracts, essential oils and hydrophobically modified pigments.

Cloud Point

The term cloud point refers to the temperature at which the compounds of formula (I) or (II) change from water soluble or clear to water insoluble or cloudy. The cloud point is determined by mixing 1 g of formula I or II in 50 g of deionized water, then, cooling the mix to 5° C. and gradually raising the temperature. The temperature at which the mixture starts to become hazy/opaque is recorded as the clouding point.

The cloud point will vary for any one compound of formula (I) or (II) depending upon the actual chemical structure of formula (I) or (II), the solvent or water used and the concentration of formula (I) or (II). The cloud point value used for purposes of this application and claim limitations is determined at a concentration of 2 wt. % in deionized water by the method described above.

The cloud point of formula (I) or (II) will likely vary once the compounds are added to the aqueous conditioning compositions. However, the cloud point limitation in the claims is based upon the standard method described above not the less predictable cloud point within a given conditioning formulation.

HLB

Hydrophilic-lipophilic balance is frequently used to measure the degree to which a molecule or surfactant is hydrophilic or lipophilic.

Delivery System

A delivery system for purposes of the invention, refers to a system which effectively delivers a hydrophobic benefit agent to skin or hair. The delivery system requires the presence of either formula (I) or (II) described above in combination with the benefit agent. An effective amount of the hydrophobic benefit agent is retained on the keratinous substrate after rinsing when said system is applied or rinsed at the cloud point of formula (I) or (II).

The delivery system will normally contain cosmetically acceptable ingredients and/or adjuvants other than water.

Rinsable Compositions

A rinsable compositions, as used herein, means a composition designed to be rinsed off by a liquid such as water. After the composition is rinsed off, the hydrophobic benefit agent(s) or the formulae (I) and/or (II) are at least in part retained on the keratinous substrate.

Keratinous Substrate

Keratinous substrate is hair, skin, scalp, finger nails or toe nails.

Cosmetic Adjuvants or Carriers Suitable for Use on Skin or Hair

Cosmetic adjuvants or carriers suitable for use on skin or hair means for example, mild surfactants or surfactants commonly use in cosmetics or personal care composition suitable for skin, super-fatting agents, consistency regulators, emulsifiers thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilizers, perfume oils, colorants, bacteria-inhibiting agents and the like.

Formula (I) and (II)

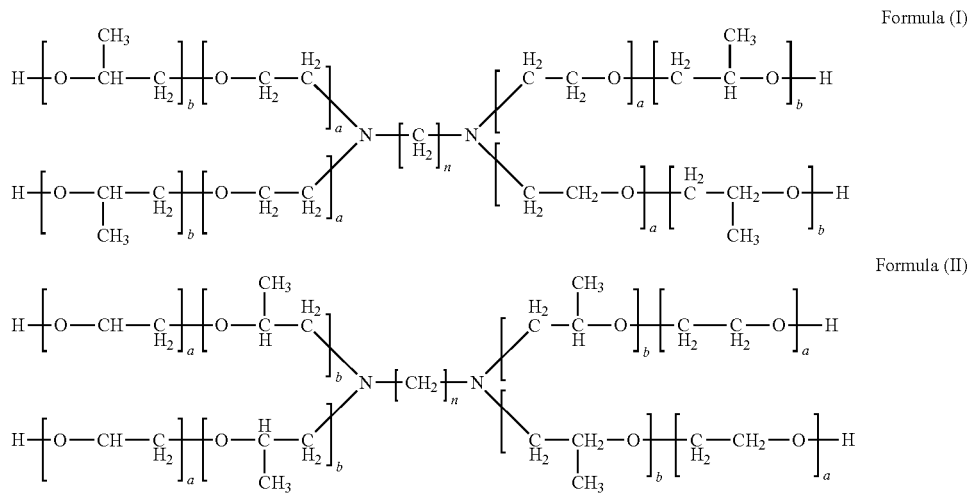

Formula (I)

Formula (II)

The only difference between formula (I) and (II) is the ethylene oxide and propylene oxide repeat units are reversed. Formula (I) is sometimes referred to a reverse Tetronic® sold by BASF Corporation. Formula (I) is especially preferred in the aqueous conditioning compositions for hair or skin.

Both of the above compounds work via cloud point to deposit directly on to hair or skin. Both compounds of formula (I) and (II), once deposited via cloud point onto hair or skin provide lubricity, emolliency and conditioning properties by themselves even in the absence of other hydrophobic agents such as silicones. Further each formula (I) or (II) functions as a delivery system for hydrophobic benefit agents to hair or skin via cloud point deposition.

In regard to formula (I) and (II), the weight percent of "a" or the ethylene oxide weight contribution may vary considerably. The weight percent of "a" is determined based on the total sum of the weight of a and b. Thus the weight % of "a" is a measure of the hydrophilic contribution of the ethylene oxide units, while the wt. % "b" measures the hydrophobic contribution of the propylene oxide units. The contributions of "a", the hydrophilic portion of formula (I) and (II) and "b", the hydrophobic portion of formula (I) and (II) are inversely proportional to one another.

Accordingly in regard to formula (I) and (II), if the wt. % of "a" varies from about 5 to about 50, preferably about 10 to about 45 and most preferably from about 15 to about 40 wt. % and the wt. % is based on the total weight of the sum of a and b repeat units, then the wt. % of "b" will vary from about 95 to 50, preferably about 90 to about 55 and most preferably from about 85 to about 60 wt. %.

The molecular weight of formula (I) and (II) varies widely from about 1,500 to about 30,000, preferably from about 2000 to about 15,000 and most preferably about 2,500 to about 12,000.

The compounds of formula (I) or (II) may be a solid, liquid or paste. Preferably the compound of formula (I) or (II) is a liquid.

The cloud point of formula (I) and (II) must be less than 100° C. However, preferably the cloud point of formula (I) and (II) ranges from about 5 to about 80° C., most preferably about 10 to about 75° C. and especially from about 12 to about 45° C.

Ideally the aqueous skin or hair conditioning compositions of formula (I) or (II) will have a cloud point at the conditions of use but may remain clear or hazy/opaque during storage. For example, when applying the aqueous conditioner formulations containing formula (I) and (II), upon rinsing with hot or warm water at temperatures between 24 and 40° C., the compounds of formula (I) and (II) will cease to be soluble in water forming polymeric micelles or other inverse phases in water. The micelles will thus deposit onto the keratinous substrate and help in deposition of hydrophobic benefit agents should a benefit agent be present or forming the conditioning film via the formula (I) or (II) alone.

The HLB will also vary widely in regard to formulae (I) and (II). Preferably the HLB will vary from about 1 to 15, preferably 1 to 10 and most preferably 1 to 7.

Applications of the Compounds of Formula (I) and (II)

The polyoxyalkylene substituted alkylene diamines of formula (I) and (II) may be used in virtually any personal care composition. The polyoxyalkylene substituted alkylene diamines of formula (I) and (II) have been found to be especially useful in aqueous personal care conditioning compositions which are used on keratinous substrates such as hair, skin or nails.

The applicants have discovered that the drying time of hair is reduced when an aqueous composition comprising a compound of formula (I) or (II) and optionally a hydrophobic benefit agent is applied to the hair and the dried, wherein the cloud point for formula (I) and formula (II) is less than 100° C., and which composition optionally further contains cosmetic adjuvants or carriers suitable for use on skin or hair. Preferably after the composition is applied to the hair it is rinsed then dried.

Fast drying time is of course a significant advantage of the aqueous compositions, preferably rinse off conditioner compositions, containing the compounds of formula (I) and (II). This improvement is especially important when the hair, human or animal hair is blow-dried. While a reduction in hair drying time per se is highly desirable, i.e. leads to less time spent in the drying process, but less drying time translates into less exposure to high temperatures of the blow-dryer. Less high temperature exposure reduces the adverse effects of that exposure.

The term reduction of the hair drying time means that the drying of hair, preferably blow drying of hair when treated with the inventive aqueous composition comprising formula (I) and (II) is at least 5%, preferably 10 or 20% lower than when the hair is treated with the base aqueous composition without compounds of formula (I) or (II), for example the base rinse off composition in Table 2 herein.

Cosmetic or Body Care Compositions Useful on Skin or Hair

There come into consideration, for example, especially the following preparations:

- skin-care preparations, e.g. skin-washing and cleansing preparations in the form of tablet-form or liquid soaps, soapless detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils;
- cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;
- foot-care preparations, e.g. foot baths, foot powders, foot creams or foot balsams, special deodorants and antiperspirants or callus-removing preparations;
- light-protective preparations, such as sun milks, lotions, creams or oils, sun blocks or tropicals, sprays and nano-materials suitable for UV protection, pre-tanning preparations or after-sun preparations;
- skin-tanning preparations, e.g. self-tanning creams;
- depigmenting preparations, e.g. preparations for bleaching the skin or skin-lightening preparations;
- insect-repellents, e.g. insect-repellent oils, lotions, sprays or sticks;
- deodorants, such as deodorant sprays, pump-action sprays, deodorant gels, sticks or roll-ons;
- antiperspirants, e.g. antiperspirant sticks, creams or roll-ons;
- preparations for cleansing and caring for blemished skin, e.g. synthetic detergents (solid or liquid), peeling or scrub preparations or peeling masks;
- hair-removal preparations in chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, aftershaves or aftershave lotions;
- fragrance preparations, e.g. fragrances (eau de Cologne, eau de toilette, eau de perfume, perfume de toilette, perfume), perfume oils or perfume creams;
- cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments and hair-structuring preparations.

Aqueous personal care compositions comprising formulae (I) and (II) are for example selected from the group consisting of hair-washing preparations in the form of shampoos and conditioners, leave on hair conditioners and rinse off hair conditioners skin-washing and cleansing preparations, body and hand lotions, body sprays, mists or gels for skin application, skin-tanning preparations sunscreens, hair-removal preparations, foot-care preparations, fragrance preparations, shaving preparations, nail creams and combinations thereof.

As implied above the personal care products can be in any form such as emulsions, creams, ointments, pastes, foams, gels, lotions, sprays, sticks or aerosols.

Creams are oil-in-water emulsions containing more than 50% of water. The oil-containing base used therein is usually mainly fatty alcohols, for example lauryl, cetyl or stearyl alcohol, fatty acids, for example palmitic or stearic acid, liquid to solid waxes, for example isopropyl-myristate or beeswax and/or hydrocarbon compounds, such as paraffin oil. Suitable emulsifiers are surfactants having primarily hydrophilic properties, such as the corresponding non-ionic emulsifiers, for example fatty acid esters of polyalcohols of ethylene oxide adducts, such as polyglycerol fatty acid ester or polyoxyethylenesorbitan fatty acid ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, preferably not more than 20 to 50%, of water or of an aqueous phase. The oil-containing phase contains predominantly hydrocarbons, such as paraffin oil and/or solid paraffin which preferably contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturizers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or preferably hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloid, for example sodium alginate, tragacanth or gum arabic. The gels preferably additionally contain also polyalcohols, such as propylene glycol or glycerol as moisturizers and wetting agents, such as polyoxyethylenesobitan fatty acid ester. The gels furthermore contain commercially available preservatives, such as benzyl alcohol, phenethyl alcohol, phenoxyethanol and the like.

As discussed above, the inventors have discovered that the compounds of formula (I) and (II) perform very well as a delivery agent for hydrophobic benefit agents. That is when formula (I) or (II) are combined in a rinse off or leave-on conditioner, a shampoo or a body wash, for skin or hair containing silicone, silicone oils, waxes, petrolatum, linear or branched oils, emollients, water insoluble or slightly soluble organic sunscreens, micronized sunscreens, lipids, ester oils, fragrances, water insoluble or slightly soluble vitamin or vitamin derivatives, plant extracts or hydrophobically modified pigments, the polyoxyalkylene substituted alkylene diamines when applied at or above the cloud point of formula (I) or (II), effectively aid in the deposition of the benefit agent onto keratinous surfaces such as hair and skin thus heightening conditioning effects.

In particular, it has been noted that the polyoxyalkylene substituted alkylene diamines effectively aid the deposition of fragrances (usually lipid soluble) onto skin or hair and help to retain the fragrance intensity over longer periods of time.

Accordingly, another embodiment of the invention is a method of prolonging the fragrance intensity on a keratinous substrate, preferably hair, skin or nails comprising the step of treating the substrate with an aqueous composition comprising a compound of formula (I) or (II) and a lipid soluble fragrance, wherein the treatment is carried out at or above the cloud point temperature of the compound of formula (I) or (II). It should also be noted that the cloud point may be reached by simply exposing the combination of formula (I) or (II) and fragrance to the body temperature of skin.

The combination of formula (I) or (II) with the benefit agent upon a slight change in temperature may form, for example a fragrance solubilizate, an aggregate, or coacervate with the benefit agent, and thus physically deposit the aggregate onto the skin or hair where the benefit agent is desired.

The present compounds of formula (I) or (II) may be used in personal care aqueous conditioning compositions at about 0.05 to about 10, preferably 0.1 to about 8 and most preferably about 0.15 to about 6 wt. % and the weight % is based on the of the total weight of the personal care aqueous conditioning composition.

In addition to the above mentioned formulae (I) and (II), the hair or skin preparations may contain further cosmetically suitable adjuvants and carriers as described below.

A particular embodiment of interest is the combination of cationic polymers and/or cationic surfactants with the polyoxylakylene substituted alkylene diamines in the aqueous conditioning compositions presently claimed.

Of special interest are cationic polymers selected from the group consisting of polyquaternium-10 (Polymer JR-40, LR-400, JR30M, and LR30M) quaternized guar gum (Jaguar® C13S. C16, Excell), acrylamidepropyl trimethyl ammonium (Salcare® SC-60) and polyquaternium 7 (Merquat® polymers, Salcare® 7) and the cationic surfactant is selected from the group consisting of cetyl trimethyl ammonium chloride or bromide, ttearalkonium chloride, Behenyl trimethyl ammonium chloride, behenyl trimethyl ammonium methosulfate, dicetyl dimonium chloride and stearamidopropyldimethylamide.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyl-dodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, iso-stearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Other Adjuvants alpha glucosylrutin (CAS No. 130603-71-3), 2-butyloctyl o-hydroxybenzoate (CAS No. 190085-41-7), vitamin E (CAS No. 1406-18-4), vitamin E acetate (CAS No. 58-95-7), diethylhexyl 2,6-naphthalate, di-n-butyl adipate, di(2-ethylhexyl)-adipate, di(2-ethylhexyl)-succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, or iminodisuccinic acid and imiondisuccinic acid salts [CAS 7408-20-0] or latex particles, aloe vera, chamomile, *ginko*

*biloba*, *ginseng*, coenzyme Q10, *laminaria ochroleuca* extract, *magnolia oborata* extract, *melalenca alternifolia* leaf oil, *rubus idaeus* seed oil, *vaccinium macrocarpon* seed oil, pumpkin seed extract, pumpkin seed oil, grape seed extract, carnosine, alpha-arbutin, madecassoside, terminolaside, tetrahydrocurcuminoids (THC), mycosporines, mycosporine like amino acids from the red alga *porphyra umbilicalis*, mycosporine-like amino acids (as described in WO2002039974), cis-9-octadecenedioic acid, lipoic acid, laurimino dipropiomic acid tocopheryl phosphates (LDTP), microcrystalline cellulose (MCC), polycarbonates as described in WO 0341676, sterols (cholesterol, lanosterol, phytosterols), as described in WO0341675 and linear poly-alpha-glucans as described in U.S. Pat. No. 6,616,935

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, *borago* oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropylene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chloride, cetyl pyridinium bromide, quaternary ammonium such as cetyltrimethylbroide ammonium bromide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene) m-block-poly(oxypropylene) n-block (oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethyl-ammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Nonionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and steareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phosphate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Cosmetically Suitable Additives

Thus the hair and skin preparations, for example creams, gels, lotions, alcoholic and aqueous/alcoholic solutions, emulsions, wax/fat compositions, stick preparations, powders or ointments, may in addition to formula (I) and (II) may contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colorants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, $\alpha$-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropyl-methylcellulose. In addition polyacrylates or homopolymer of reticulated acrylic acids and poly-acrylamides, carbomer (carbopol types 980, 981, 1382, ETD 2001, ETD2020, Ultrez 10) or Salcare range such as Salcare SC80 (steareth-10 allyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), associative thickeners Luvigel Start (Polyurethane/39), Arlypon TT (PEG/PPG/120\10 Trimethylolpropane trioleate laureth-2), cationic liquid dispersion polymers such as Salcare SC96 (Polyquaternium-37 (and) Propylene Glycol Dicaprate Dicaprylate (and) PPG-1 Trideceth-6), and Cosmedia Triple C (Polyquaternium-37 (and) dicaprylyl carbonate (and) lauryl glucoside), etc.

Polymers

Suitable cationic polymers are, for example, cationic cellulose derivatives, for example a quaternized hydroxymethyl cellulose obtainable under the name Polymer JR 400 from Amerchol, cationic starches, copolymers of diallylammonium salts and acrylamides, quarternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat® L/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert-butylaminoethyl methacrylate/2-hydroxypropyl methacrylate copolymers, polyvinylpyrrolidone, vinyl pyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2, 4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in WO 0025731:

Structures 1-3 (page 2), structure 4 (page 6), structures 5-6 (page 7) and compounds 7-33 (page 8-14).

The amount of antioxidants present is usually from 0.001 to 30% by weight, preferably from 0.01 to 3% by weight, based on the weight of the UV absorber of formula (1).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glycerine, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan® and further substance classes listed in the following reference: K. F. DePolo—A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petit-grain), from fruit (aniseed, coriander, carraway, juniper), from fruit peel (bergamot, lemons, oranges), from roots (mace, *angelica*, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (*galbanum*, elemi, benzoin, myrrh, olibanum, opoponax). Animal raw materials also come into consideration, for example civet and castoreum.

Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, *galbanum* oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenyl acetic acid, geranyl acetate, benzyl acetate, rose oxide, romillat, irotyl and floramat alone or in admixture with one another.

Colorants

There may be used as colorants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colorants are usually used in concentrations of from 0.001 to 0.1% by weight, based on the total mixture.

Other Adjuvants

It is furthermore possible for the hair and skin preparations to contain, as adjuvants, anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Thus the hair and skin preparations, may in addition to formula (I) and (II) contain mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colorants, bacteria-inhibiting agents and the like.

Examples

TABLE 1

Chemical Composition and Characteristics of Formulae (I) and (II) Tested in Application Examples. Note samples 1-10 are available from BASF Corporation under the tradename Tetronics ®.

| Sample | Formula (I)/(II) | Cloud Point/[2] ° C. | HLB | wt. % EO-% PO[3] | [1]Mw |
|---|---|---|---|---|---|
| 1 Tetronic ® 304 | (II) | 75 | 12-18(16) | 54-46 | 1650 |
| 2 Tetronic ® 701 | (II) | 18 | 1-7(3) | 16-84 | 3600 |
| 3 Tetronic ® 901 | (II) | 20 | 1-7(3) | 16-84 | 4700 |
| 4 Tetronic ® 904 | (II) | 74 | 15 | 47-53 | 6700 |
| 5 Tetronic ® 908 | (II) | >100 | >24(31) | 86-14 | 25000 |
| 6 Tetronic ® 1107 | (II) | >100 | 18-23(24) | 72-28 | 15000 |
| 7 Tetronic ® 1301 | (II) | 16 | 1-7(2) | 16-84 | 6800 |
| 8 Tetronic ® 1307 | (II) | >100 | >24(24) | 73-27 | 18000 |
| 9 Tetronic ® 90R4 | (I) | 43 | 1-7(7) | 48-52 | 6900(7240) |
| 10 Tetronic ® 150R1 | (I) | 18-20 | 1-7(1) | 17-83 | 8000 |
| 11 | (I) | 18-20 | 1-7 | 27-73 | 8000 |
| 12 | (I) | 18-20 | 1-7 | 37-63 | 8000 |

[1]Mw is weight average molecular weight and is determined by hydroxyl number using a phthalic anhydride-imidazole method. The polyol is dissolved in pyridine-phthalic anhydride solution. Under reflux, OH groups in the polyol are esterified with phthalic anhydride. Water is then added to release the excess anhydride as phthalic acid. The excess phthalic acid is then titrated with 0.5N KOH to a colormetric or potentiometric endpoint. The volume of KOH consumed is a measure of the hydroxylnNumber of the polyol expressed as mg KOH/gram.

[2]The cloud point is determined by mixing 1 g of formula I or II in 50 g of deionized water, then, cooling the mix to 5° C. and gradually raising the temperature. The temperature at which the mixture starts to become hazy/opaque is recorded as the clouding point.

[3]The % EO-% PO percent is based on the total weight of EO and PO repeat units.

Applications Examples

Conditioning Formulations Containing Formula (I) or (II) Samples in Table 1

5.0 g hair tresses 8 inches of mulato origin are treated with a rinse-off crème conditioning formulation as below.

TABLE 2

Rinse off Crème Conditioning Formulation

| Phase | Component | Wt. % |
|---|---|---|
| 1 | Samples 1-10 | 4 |
|   | Lanette ® O | 3 |
|   | Cetyl Alcohol | 3 |
|   | Polawax | 3 |
|   | Cremophor ® A6 | 1.5 |
|   | Cremophor ® A25 | 0.5 |
| 2 | De-ionized water | q.s to 100% |
| 3 | Germaben ® II | 0.5 |
|   | Citric acid | 0.2 |

The hair tresses are wetted with water at 35° C. Shampoo is then applied via pipette with gentle rubbing onto the hair gently until foam was produced for 30 seconds. Rinsing is carried out by stroking the hair gently with the fingers while the hair is placed in a flow of tap water at 35 C for 30 seconds. The water flow is approximately adjusted to 2.0 gpm (gallons per minute). 1 g of the above rinse-off crème conditioner containing 4 wt. % of samples 1-12 (see Table 1)

Substantivity Test

A basic dye (lumicresaux from Clariant) is used to analyze for substantivity of the conditioner formulations according to Table 1 above containing formula (I) or (II) (samples 1-12).

The method for evaluating substantivity consists of immersing the treated hair tresses as above in a dye solution of 0.1% of lumicreasaux at a pH of ~3.0 for 60 seconds, and then, rinsing for 30 seconds. This dye forms complexes with the weak amine groups of the compounds of formula (I) and (II) and reveals the presence or absence of compounds of formula (I) or (II) on the hair surface. Extraction of the dye from the hair is made with a solution of 50% water and 50% IPA. A subjective scale of 1-7 is used to assess for level of purple/reddish complex extracted from the hair surface.

The criteria used for analysis is as follows: 1=no color and no substantivity; 7=very intense color, and substantivity with full coverage. Within this scale, the stronger the color of the extracted solution (higher numbers), the higher formula (I) and (II) substantivity to hair.

Work Load Reduction Test

The method used for determining the % work load reduction energies are measured by using a Diastron Tensile Tester 660.

The tress is washed with 1 g of 27% SLES-2 and then placed on the dia-stron holder and manually combed out using both ends of the comb. The tress is then rinsed and placed on the Dia-stron for evaluation. Each tress is treated with 1 g of the sample and evaluated against the control. The two data sets (control and sample) are evaluated.

TABLE 3

Results of Substantivity of Samples 1-12 of Formulae (I) or (II) to Hair and Reduction in Work Load at Temperatures of <16.4° C. and >23.0° C. Using the Dia-stron Tensile Tester 660.

| Sample | Cloud Point ° C. | Dye intensity at T <16.4° C. | Dye intensity at T >23.0° C. | Work load reduction at <16.4° C. | Work load reduction at >23.0° C. |
|---|---|---|---|---|---|
| 1 | 75 | 1 | 2 | −5 | 5 |
| 2 | 18 | 2 | 4 | 4 | 35 |
| 3 | 20 | 2 | 4 | 6 | 42 |
| 4 | 74 | 1 | 2 | 4 | −10 |
| 5 | >100 | 2 | 1 | −5 | 6 |
| 6 | >100 | 2 | 1 | 4 | 12 |
| 7 | 16 | 1 | 4 | 10 | 32 |
| 8 | >100 | 1 | 2 | −7 | 8 |
| 9 | 43 | 2 | 3 | 8 | −9 |
| 10 | 18-20 | 1 | 7 | 2 | 75 |
| 11 | 18-20 | 2 | 6 | −3 | 68 |
| 12 | 18-20 | 2 | 6 | 2 | 67 |

The dye intensity increased for all samples 1-12 (Table 1) when the conditioner was applied at temperatures above 23.0° C.

TABLE 4

Relationship Between Temperature of Use and % Work Load Reduction is Determined for Samples 10-12 (cloud points between 18-20).

| Application Temperature | Sample 10 % Work Load Reduction | Sample 11 % Work Load Reduction | Sample 12 % Work Load Reduction |
|---|---|---|---|
| 0 | 0 | 0 | 0 |
| 5 | 5 | 5 | 2 |
| 10 | 5 | 5 | 2 |
| 15 | 18 | 12 | 9 |
| 20 | 55 | 55 | 40 |
| 25 | 72 | 70 | 55 |
| 30 | 75 | 71 | 62 |
| 35 | 75 | 70 | 65 |
| 40 | 75 | 72 | 68 |

Deposition of Fragrance and Retained Intensity Over Time

A gel conditioner formulation containing sample 10 verses Behenyl TMS-50 are compared for prolonging fragrance intensity on hair.

Gel Crème Conditioner

4% Samples 10, 11, 12 and Behenyl TMS

1% Cetiol® C5

0.5% Carbomer 0.3% AMP-Ultra PC-2000

0.1% Citric Acid q.s. to 100% with de-ionized water

Behenyl TMS and sample 10 are added at 4 wt. % to the above formulation and their activity compared as below in Table 5. The gel crème conditioner is applied to hair and rinsed essentially as described above.

The effect on fragrance intensity is monitored over 8 hours

TABLE 5

Fragrance Intensity verses Time in Hours of Sample 10 vs. Behenyl TMS.

| | 4 wt. % Sample 10 | |
|---|---|---|
| Time in Hours | Fragrance Intensity | 4 wt. % Behenyl TMS Fragrance Intensity |
| 0 | 7 | 7 |
| 2 | 6 | 2 |
| 4 | 5 | .5 |
| 6 | 4.5 | 0 |
| 8 | 4 | 0 |

From the tables above it is very clear that when compounds of formula (I) or (II) are used in conditioning formulations, they provide work load reduction, substantivity to hair and the ability to deposit hydrophobic benefit agents such as lipid soluble fragrances. Furthermore, the samples according to the invention also prolong the intensity of a fragrance on hair.

Deposition of Sunflower Seed Oil from Hair Conditioners onto European Brown Hair Four samples are prepared using the base conditioner below.

Sample A is the control which contains only the base conditioner (no sun flower seed oil).

Sample B is base conditioner and 5 wt. % of the sun flower seed oil only.

Sample C is base conditioner and 5 wt. % sunflower seed oil and sample 10 according to the invention.

Sample D is base conditioner and 5 wt. % sun flower seed oil and 5 wt. % Behenyl TMS.

TABLE 7

Formulation of Sample B

| | Ingredient | Percent (%) | Amount In Batch (g) |
|---|---|---|---|
| 1 | Lanette O | 3.00% | 9.00 |
| 2 | Lanette ® 16 | 3.00% | 9.00 |
| 3 | Cremophor ® A25 | 0.50% | 1.50 |
| 4 | Cremophor ® A6 | 1.50% | 4.50 |
| 5 | Polawax | 3.00% | 9.00 |
| 6 | Germaben ® II | 0.50% | 1.50 |
| 7 | Citric Acid | 0.20% | 0.60 |
| 8 | Lipovol ® Sun (SFSO) | 5.00% | 6.00 |
| 9 | De-ionized Water | 86.30% | 258.90 |
| | Total | 100.00% | 300 g |

TABLE 8

Formulation of Sample C

| | Ingredient | Percent (%) | Amount In Batch (g) |
|---|---|---|---|
| 1 | Lanette ® O | 3.00% | 9.00 |
| 2 | Lanette ® 16 | 3.00% | 9.00 |
| 3 | Cremophor ® A25 | 0.50% | 1.50 |

TABLE 8-continued

Formulation of Sample C

| | Ingredient | Percent (%) | Amount In Batch (g) |
|---|---|---|---|
| 4 | Cremophor ® A6 | 1.50% | 4.50 |
| 5 | Polawax | 3.00% | 9.00 |
| 6 | Germaben ® II | 0.50% | 1.50 |
| 7 | Citric Acid | 0.20% | 0.60 |
| 8 | Lipovol ® Sun (SFSO) | 5.00% | 6.00 |
| 9 | Sample 10 | 5.00% | 15.00 |
| 10 | De-ionized Water | 81.30% | 258.90 |
| | Total | 100.00% | 300 g |

TABLE 9

Formulation of Sample D

| | Ingredient | Percent (%) | Amount In Batch (g) |
|---|---|---|---|
| 1 | Lanette ® O | 3.00% | 9.00 |
| 2 | Lanette ® 16 | 3.00% | 9.00 |
| 3 | Cremophor ® A25 | 0.50% | 1.50 |
| 4 | Cremophor ® A6 | 1.50% | 4.50 |
| 5 | Polawax | 3.00% | 9.00 |
| 6 | Germaben ® II | 0.50% | 1.50 |
| 7 | Citric Acid | 0.20% | 0.60 |
| 8 | Lipovol ® Sun (SFSO) | 5.00% | 6.00 |
| 9 | Behenyl TMC | 5.00% | 15.00 |
| 10 | De-ionized Water | 81.30% | 258.90 |
| | Total | 100.00% | 300 g |

1-2 g European brown hair tresses are washed with approximately 1 gram of 5% SLES-2 for 30 seconds and then rinsed for 30 seconds with water. 1 g of conditioner is applied for 30 seconds and rinsed for 30 seconds with tap water at 32-37° C. Tresses are left to dry.

All treated tresses are placed in 25 ml of heptane in 50 ml centrifuge tubes and then the tubes are placed on the vortex at 1000 RPM for 10 minutes and then analyzed by gas chromatography for amount of sun flower seed oil.

TABLE 10

Results of Sun Flower Seed Oil Deposition on Hair

| Sample | Wt. of Hair | SFSO Deposition (ppm) from 25 ml solution | Calculated deposition on hair (ppm) |
|---|---|---|---|
| [1]Base Conditioner (#1) Control | 1.32 | 2 | 37.88 |
| Base Conditioner (#2) | 1.35 | 2 | 37.04 |
| Base Conditioner (#3) | 1.39 | 2 | 35.97 |
| Sample B (#1) | 1.35 | 2 | 37.04 |
| Sample B (#2) | 1.15 | 98 | 2130.43 |
| Sample B (#3) | 1.08 | 36 | 833.33 |
| Sample C (#1) | 1.53 | 90 | 1470.59 |
| Sample C (#2) | 1.71 | 93 | 1359.65 |
| Sample C (#3) | 1.26 | 90 | 1785.71 |
| Sample D (#1) | 1.27 | 8 | 157.48 |
| Sample D (#2) | 1.46 | 13 | 222.60 |
| Sample D (#3) | 1.31 | 15 | 286.26 |

[1]Base conditioner is without sun flower seed oil (SFSO).
2. The Sample C according to the invention also appears to stabilize the SFSO.

All conditioners that contained the sunflower seed oil deposit the oil on to hair. Sample C according to the invention has the strongest deposition on hair.

Stability Testing of Various Formulations Containing the Polyoxyalkylene Substituted Alkylene Diamines Formulations below containing samples 1-12 in Table 1 are tested for stability at 45° C. for 3 months. All are shown to be stable under these conditions.

Gel Conditioner
3.0% samples 1-12
2.5% Hydroxyethyl Cellulose
2.5% Acrylcopolymer GK 2518162
q.s. to 100 with de-ionized water Rinse-Off CrèMe Conditioner
Phase 1
4% Samples 1-12
3% Lanette® O
3% Cetyl Alcohol (Crodacol-C95)
3% Polawax
1.5% Cremophor® A6
0.5% Cremophor® A25
Phase 2
q.s. to 100% with de-ionized water
Phase 3
0.5% Germaben® II
0.2% Citric Acid Rinse-Off CrèMe Conditioner
Phase 1
3% Lanette® O
3% Cetyl Alcohol (Crodacol-C95)
3% Polawax
1.5% Cremophor® A6
0.5% Cremophor® A25
Phase 2
4% Samples 10-12
q.s. to 100% with de-ionized water
Phase 3

Gel Crème Conditioner
4% samples 10-12
1% Cetiol C5
0.5% Carbomer
0.3% AMP-Ultra PC-2000
0.1% Citric Acid
q.s. to 100% with de-ionized water Drying Behavior of Hair Using the Sample 10

To determine the drying potential of the rinse-off conditioners containing the test samples, approximately 4.5 g/8 in. hair swatches of virgin, medium brown European hair is subjected to a washing protocol that consisted of a one minute rinse in warm (35° C.) tap water, one minute wash/lather with a solution of 12% sodium laureth-2 sulfate and 3% cocamidopropyl betaine (0.1 g/g hair), and one minute rinse in warm tap water. The test conditioners of the formula shown in Table 11 are then applied and left on the hair for one minute and then rinsed for one minute. Excess water is removed by running the hair through two fingers and combing through with the wide tooth side of a wide/fine dual tooth comb five times. Additional excess water is removed by blotting the tip of the hair swatch as drops formed. The final weight of all wet hair swatches is approximately 58% greater than the weight of the dry hair swatches. The hair swatches are then blow dried with a ConairPro Yellowbird blow dryer equipped with a 5.5 in. wide ConairPro diffuser attachment in one-minute increments up to a total of six minutes. The blow dryer is positioned approximately 2.5-3.0 in. from the vertical hair swatch and set to "medium heat" (≈55° C.) and "high" air flow. The hair is weighed following each minute increment and combed through with a wide tooth comb only after the two and four minute time points.

The percent weight change from the original dry state is plotted against blow dry time to illustrate the drying behavior of hair. The percent weight change from dry state after four minutes of blow drying, the point at which the bulk of the hair reached an acceptable dry feel and contained less than 10% added water, and the resulting rate of drying are tabulated in Table 12. The data indicate that Sample 10 can provide a hair drying benefit, e.g. increased rate of drying, when formulated in a rinse-off crème conditioner. This benefit is not observed when Sample 10 was excluded from the formulation (control).

TABLE 11

Rinse-off Crème Conditioning Base Formula (Control).

| Phase | Component | Wt. % |
|---|---|---|
| 1 | Lanette ® O | 3.00 |
|  | Lanette ® 16 | 3.00 |
|  | Polawax | 1.50 |
|  | Cremophor ® A6 | 1.50 |
|  | Cremophor A25 | 1.25 |
| 2 | Deionized water | q.s. to 100% |
| 3 | Citric acid | q.s. to pH 5.50 ± 0.50 |
|  | Kathon CG | 0.10 |
|  | Fragrance | 0.50 |

TABLE 12

Drying Behavior of Virgin Hair

| Blow Dry Time (min.) | Mean Percent Weight Change from Dry State (%; mean ± SD; n = 3) | | |
|---|---|---|---|
|  | Control | 4 wt. % Sample 10 | 10 wt. % Sample 10 |
| 0 | 57.9 ± 0.6 | 57.8 ± 0.1 | 56.8 ± 0.3 |
| 1 | 45.9 ± 2.3 | 46.1 ± 1.5 | 46.0 ± 1.2 |
| 2 | 36.0 ± 3.0 | 35.3 ± 3.1 | 34.5 ± 2.6 |
| 3 | 22.8 ± 2.3 | 20.0 ± 4.0 | 19.5 ± 3.6 |
| 4 | 11.6 ± 1.2 | 7.1 ± 3.8 | 7.1 ± 1.4 |
| 5 | 2.4 ± 1.0 | −0.2 ± 0.6 | −0.9 ± 0.8 |
| 6 | −1.3 ± 1.0 | −2.1 ± 0.5 | −2.5 ± 1.1 |
| Reduction in Percent Weight Change from Dry State after 4 min. (%) | 46.3 ± 1.3 | 50.7 ± 3.8 | 49.7 ± 1.1 |
| Hair Drying Rate over 4 min. (Reduction in Percent Weight Change from Dry State/min.) | 11.6 ± 0.3 | 12.7 ± 0.9 | 12.4 ± 0.3 |

The invention claimed is:

1. An aqueous hair or skin conditioner composition comprising a compound of formula (I)

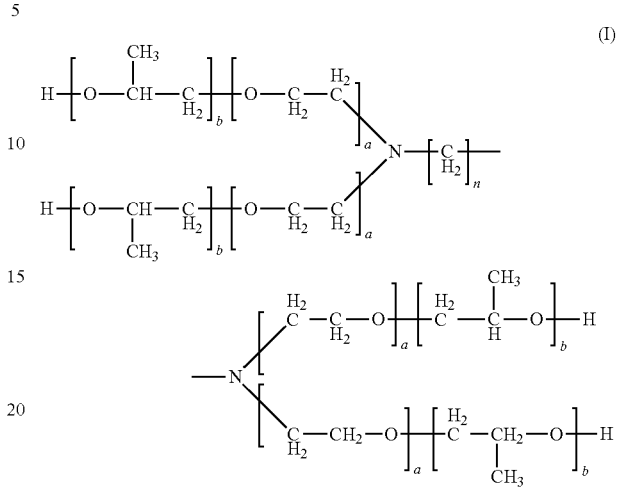

wherein
a and b represent ethylene oxide and propylene oxide repeat units, respectively;
n is 1-4; and
wherein the ethylene oxide repeat units are 17, 27, or 37 wt. % of the sum of the ethylene oxide and propylene oxide repeat units; and
wherein
the aqueous composition comprises from about 0.05 to about 10 wt. % of the compound of formula (I) and from about 10 to about 95 wt. % water, based on the total weight of the composition; and
the compound of formula (I) has a weight average molecular weight of 8,000, a cloud point of from about 18-20° C. and an HLB from 1 to 7;
wherein the cloud point is determined by mixing 1 g of formula (I) in 50 g of deionized water, followed by cooling the mixture to a temperature of 5° C. and gradually raising the temperature until the cloud point is reached.

2. The aqueous hair or skin conditioner composition according to claim 1, wherein n is 2.

3. The aqueous hair or skin conditioner composition according to claim 2, wherein the rinse-off or leave-on conditioners are selected from the group consisting of hair conditioning crème rinses, leave on hair conditioners, setting lotions, blow-drying lotions, restructuring lotions, styling gels, cleansing products for skin selected from the group consisting of body and hand lotions, body sprays, mists or gels for skin application, body washes, sunscreens, shaving creams, after-shave, after-shave moisturizers, depilatory creams, nail creams and combinations thereof.

4. The aqueous hair or skin conditioner composition according to claim 1, wherein the composition is in the form of an emulsion, cream, ointment, paste, form, gel, lotion, spray, stick or aerosol.

5. The aqueous hair or skin conditioner composition accordingly to claim 1, wherein the composition is in the form of a water-in-oil or oil-in-water emulsion.

6. The aqueous hair or skin conditioner composition according to claim 1, wherein the composition excludes surfactants above an HLB of 25.

7. The aqueous hair or skin conditioner composition according to claim 1, wherein the composition further comprises a viscosifying or structuring agent or polymer.

8. The aqueous hair or skin conditioner composition according to claim 1, wherein the composition further comprises a hydrophobic benefit agent selected from the group consisting of fatty alcohols, esters of fatty acids, hydrophobic vitamin or vitamin complexes, natural or synthetic triglycerides, pearlescent waxes, hydrocarbon oils, siloxanes or silicones, perfume oils, super-fatting agents, water insoluble or slightly soluble organic sunscreens, micronized sunscreens, plant extracts, essential oils and hydrophobically modified pigments.

9. The aqueous hair or skin conditioner composition according to claim 1, where a concentration of the compound of formula (I) in the composition is from about 0.1 to about 8 wt. %, based on the total weight of the composition.

10. The aqueous hair or skin conditioner composition according to claim 1, which further contains a cationic polymer and/or cationic surfactant.

11. The aqueous hair or skin conditioner composition according to claim 10, comprising a cationic polymer selected from the group consisting of polyquaternium-10, quaternized guar gum, acrylamidepropyl trimethyl ammonium and polyquaternium 7 and a cationic surfactant selected from the group consisting of cetyl trimethyl ammonium chloride or bromide, tetraalkonium chloride, behenyl trimethyl ammonium chlorides, behenyl trimethyl ammonium methosulfate, dicetyl dimonium chloride and strearamidopropyldimethylamine.

12. A method of conditioning a keratinous substrate comprising the step of treating the substrate with an aqueous composition according to claim 1, wherein the substrate treatment step is carried out at a temperature at or exceeding the cloud point of the compound of formula (I).

13. A method of reducing a drying time for hair comprising the steps of applying to the hair an aqueous composition according to claim 1 and drying the hair.

14. The method according to claim 13, wherein the method includes a rinsing step between applying and drying the hair.

* * * * *